(12) United States Patent
Yamamoto et al.

(10) Patent No.: US 7,399,836 B2
(45) Date of Patent: Jul. 15, 2008

(54) METHOD OF MANUFACTURING A CARRIER HAVING IMMOBILIZED ANTIBODIES

(75) Inventors: Akira Yamamoto, Tokyo (JP); Ken Sugo, Saitama-ken (JP)

(73) Assignee: HOYA Corporation, Tokyo (JP)

( * ) Notice: Subject to any disclaimer, the term of this patent is extended or adjusted under 35 U.S.C. 154(b) by 106 days.

(21) Appl. No.: 11/201,379

(22) Filed: Aug. 11, 2005

(65) Prior Publication Data

US 2006/0051342 A1    Mar. 9, 2006

Related U.S. Application Data

(63) Continuation of application No. 09/994,784, filed on Nov. 28, 2001, now abandoned.

(30) Foreign Application Priority Data

Nov. 29, 2000    (JP) .............................. 2000-362762

(51) Int. Cl.
   *C07K 16/00*    (2006.01)
(52) U.S. Cl. ................................... 530/387.1
(58) Field of Classification Search ........................ None
   See application file for complete search history.

(56) References Cited

U.S. PATENT DOCUMENTS

| | | | |
|---|---|---|---|
| 4,885,207 A | 12/1989 | Johnson et al. | |
| 5,540,995 A | 7/1996 | Kitano et al. | |
| 5,827,669 A | 10/1998 | Nakayama et al. | |
| 5,897,953 A | 4/1999 | Ogawa et al. | |
| 6,040,196 A | 3/2000 | Mitoh et al. | |

FOREIGN PATENT DOCUMENTS

| | | |
|---|---|---|
| EP | 1074616 | 2/2001 |
| GB | 2282548 | 4/1995 |
| GB | 2293009 | 3/1996 |
| GB | 2307552 | 5/1997 |
| JP | 64-38657 | 2/1989 |
| JP | 2001-133459 | 5/2001 |

OTHER PUBLICATIONS

English Langauge Abstract of EP 1074616.
English Langauge Abstract of JP 64-38657.

*Primary Examiner*—Michail A Belyavskyi
(74) *Attorney, Agent, or Firm*—Greenblum & Bernstein, P.L.C.

(57) ABSTRACT

Carrier and method of its manufacture having immobilized antigens or antibodies, including a carrier having a surface, in which at least the surface of the carrier is formed of a calcium phosphate based compound; antiligands provided on and surrounding the surface of the carrier; a blocking layer formed of a protein having low interaction with antigens or antibodies, the blocking layer being formed on a portion of the surface of the carrier where the antiligands are not provided; and antigens or antibodies each having a portion that is irrelevant to the antigen-antibody reaction on which a ligand is provided, the antigens or antibodies being immobilized to the surface of the carrier through the bonding between the ligands and the antiligands with the blocking layer effectively preventing antigens or antibodies from being directly absorbed to the surface without bonding between the ligands and the antiligands.

19 Claims, 1 Drawing Sheet

METHOD OF MANUFACTURING A CARRIER HAVING IMMOBILIZED ANTIBODIES

CROSS-REFERENCE TO RELATED APPLICATION

Figure 1:
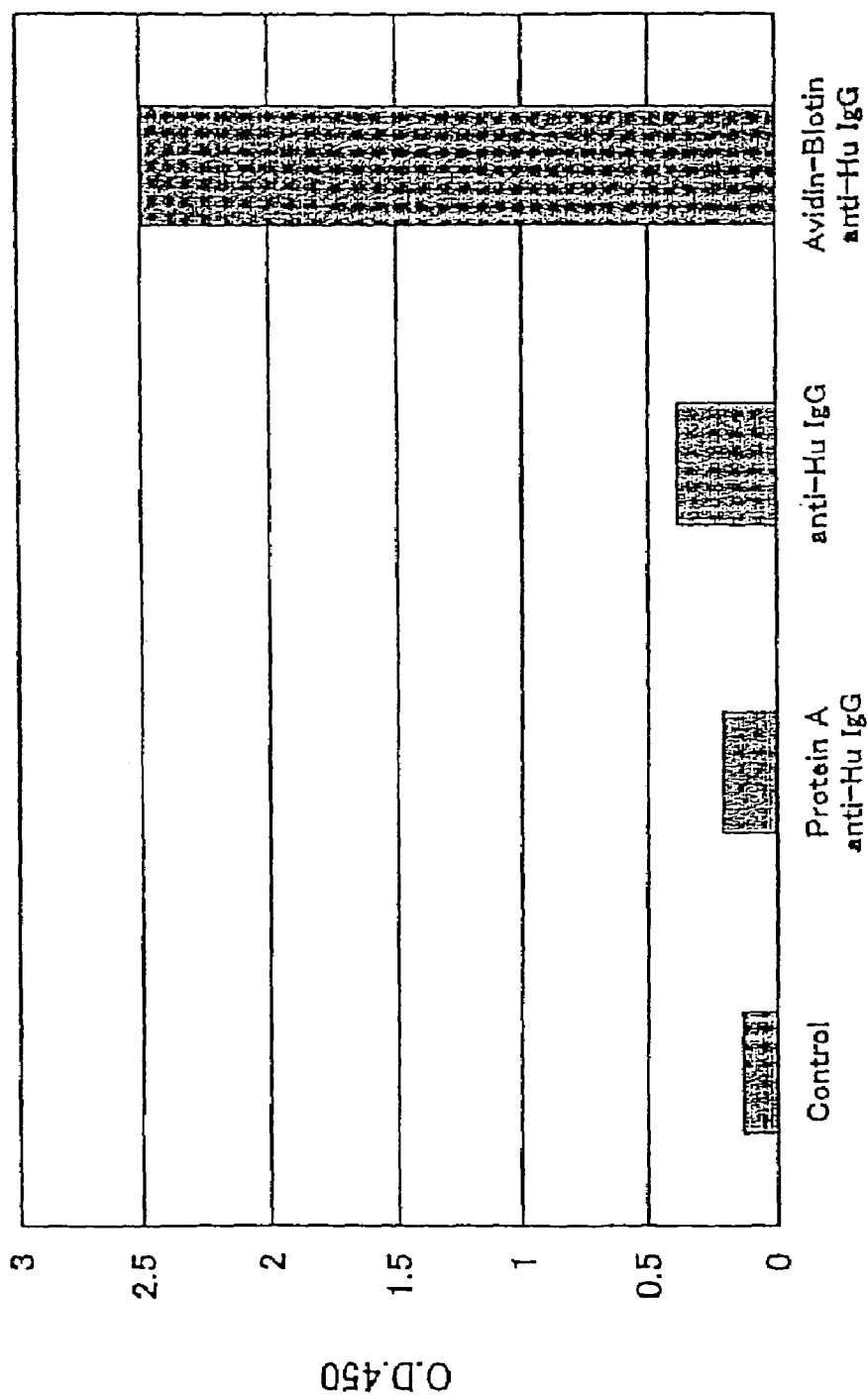

This application is a continuation of application Ser. No. 09/994,784, filed Nov. 28, 2001 now abandoned, which is hereby incorporated by reference in its entirety. The present application claims priority under 35 U.S.C. § 119 of Japanese Application No. 2000-362762 filed Nov. 29, 2000, the disclosures of which is expressly incorporated by reference herein in its entirety.

BACKGROUND OF THE INVENTION

1. Field of the Invention

The present invention relates to a carrier having immobilized antigens or antibodies which is useful in diagnosing various diseases such as infectious utilizing the antigen-antibody reaction, and a method of manufacturing thereof. Note that, in the following description, the carrier having immobilized antigens or antibodies is also referred to as "a carrier to which antigens or antibodies are immobilized".

2. Description of the Prior Art

It is known that calcium phosphate compounds have a characteristic that adsorbs not only antibodies but also proteins and their conjugated proteins that could be various antigens. Because of this characteristic, it is believed that one that is obtained by immobilizing (adsorbing) antigens or antibodies to a calcium phosphate compound can be utilized to various antigen-antibody reactions.

In recent years, for diagnosing various diseases such as infectious, various considerations have been made to a method in which after immobilizing antigens or antibodies to a carrier made of a calcium phosphate compound, a sample to be examined is made contact with the carrier to observe an agglutination image caused by the antigen-antibody reaction.

However, a sufficient reaction does not occur by simply immobilizing the antigens or antibodies to the carrier due to poor bonding ability between the carrier and the antigens or antibodies (bonding objects) in the examined sample.

SUMMARY OF THE INVENTION

It is therefore an object of the present invention to provide a carrier having immobilized antigens or antibodies which has a high bonding ability with antigens or antibodies (bonding objects) in the sample to be examined, and a method for manufacturing thereof.

In order to achieve the above-mentioned object, the present invention is directed to a carrier having immobilized antigens or antibodies, comprising a carrier having a surface which is formed of a calcium phosphate based compound, and antigens or antibodies each having a portion that is irrelevant to the antigen-antibody reaction, each of said antigens or antibodies being immobilized to the surface of the carrier through the irrelevant portion thereof, wherein the surface of the carrier has a portion where the antigens or antibodies are not immobilized, and at least a part of the portion of the surface is coated with a protein having low interaction with antigens or antibodies.

According to the present invention, it is possible to provide a carrier having immobilized antigens or antibodies which has high bonding ability to antigens or antibodies (bonding objects) in a sample to be examined.

In this invention, it is preferred that the carrier carries antiligands thereon and each antigen or antibody has a ligand bonded thereto, in which each antigen or antibody is immobilized to the carrier through the ligand and the antiligand. This makes it possible to immobilize the antigens or antibodies to the carrier while maintaining the high bonding ability to the antigens or antibodies in the sample to be examined.

Further, it is preferred that each antiligand is carried by the surface of the carrier by adsorption. This makes it possible to produce the carrier having immobilized antigens or antibodies.

In this case, it is preferred that each antibody has a constant region, and the ligand is bonded to the constant region of the antibody. According to this feature, the antigens become more preferably bonded to the antibodies.

Furthermore, it is preferred that the coating of the protein is made by adsorption of the carrier to the part of the portion of the surface. According to this feature, it becomes possible to easily carry out the coating of the surface of the carrier.

Further, in the present invention, it is preferred that the protein is casein. Casein is the most preferable protein (coating material) as the coating substance for the carrier.

Furthermore, in the present invention, it is preferred that the antigens or antibodies are stabilized. This makes it possible to prevent the carrier having immobilized antigens or antibodies from being deteriorated with the elapse of time.

In this case, it is preferred that the antigens or antibodies are stabilized by treating the carrier with a stabilizing agent. This is the most simple and effective method for stabilizing the antigens or antibodies.

Further, in the present invention, it is preferred that the antigens or antibodies are stabilized by treating the carrier with a cross-linking agent which cross-links the antigens or antibodies and the ligands and/or antiligands. This makes it possible to prevent the antigens or antibodies from being removed from the carrier more reliably.

In this case, it is preferred that the cross-linking agent is a bivalent cross-linking agent. This makes it possible to stabilize the antigens or antibodies more reliably.

Furthermore, in the present invention, it is preferred that a portion of the carrier which is in the vicinity of the surface thereof is formed into a dense structure. This makes it possible to immobilize the antigens or antibodies such that their reacting parts are far from the surface of the carrier through the substantially same distance.

Moreover, in the present invention, it is preferred that the carrier includes a carrier body having a surface thereof, and a coating made of a calcium phosphate based compound and provided on the surface of the carrier body. According to this feature, it is possible to adjust the density of the carrier having immobilized antigens or antibodies so as to be the optimum condition for the agglutination reaction.

In this case, it is preferred that the carrier is produced by colliding porous particles of the calcium phosphate based compound to the carrier body. This makes it possible to easily and reliably form the vicinity of the surface of the carrier into dense structure.

Further, in this case, it is also preferred that the porous particles are produced by agglutination bonding of primary particles of the calcium phosphate based compound. This makes it possible to more easily form the vicinity of the surface of the carrier into dense structure.

Moreover, in the present invention, it is preferred that the antibodies are IgG. This makes it possible to increase the degree of selection of antigens.

Another aspect of the present invention is directed to a method of manufacturing a carrier having immobilized antigens or antibodies, the method comprising the steps of: an immobilizing step for immobilizing antigens or antibodies to a surface of a carrier which is formed of a calcium phosphate based compound through portions of the antigens or antibodies that are irrelevant to the antigen-antibody reaction, and a coating step for coating at least a part of a portion of the surface of the carrier, where the antigens or antibodies are not immobilized, with a protein having low interaction with antigens or antibodies.

According to the invention, it is possible to provide a manufacturing method of a carrier having immobilized antigens or antibodies which has high bonding ability to antigens or antibodies (bonding objects) in a sample to be examined.

In this method, it is preferred that the immobilizing step includes: a step of letting antiligands to be carried on the surface of the carrier; and a step of contacting antigens or antibodies to which ligands having affinity to the antiligands are bonded, to the carrier. This makes it possible to immobilize the antigens or antibodies to the carrier while maintaining the high bonding ability to the antigens or antibodies in the sample to be examined.

Further, in this method, it is preferred that the antiligands are carried on the carrier by being adsorbed by the surface of the carrier. This makes it easy to manufacture the carrier having immobilized antigens or antibodies.

Furthermore, it is also preferred that the ligands are bonded to constant regions of the antibodies. According to this feature, the antigens become more preferably bonded to the antibodies.

Moreover, in this method, it is also preferred that the coating step is carried out by letting the protein to be adsorbed to the part of the portion of the surface of the carrier. This makes it possible to easily carry out the coating of the surface of the carrier.

Further, in this method, it is also preferred that the protein is casein. Casein is the most preferable protein (coating material) as the coating substance for the carrier.

Furthermore, in this method, it is preferred that the method further comprises, after the immobilizing step, a step of stabilizing the antigens or antibodies. This makes it possible to prevent the carrier having immobilized antigens or antibodies from being deteriorated with the elapse of time.

In this case, it is preferred that the stabilizing step is carried out by treating the carrier with a stabilizing agent. This is the most simple and effective method for stabilizing the antigens or antibodies.

Further, in this method, it is preferred that the stabilizing step is carried out by treating the carrier with a cross-linking agent for bonding the antigens or antibodies to the ligands and/or antiligands. This makes it possible to prevent the antigens or antibodies from being removed from the carrier more reliably.

In this case, it is preferred that the cross-linking agent is a bivalent cross-linking agent. This makes it possible to stabilize the antigens or antibodies more reliably.

Furthermore, in this method, it is preferred that a portion of the carrier which is in the vicinity of the surface thereof is formed into a dense structure. This makes it possible to immobilize the antigens or antibodies such that their reacting parts are far from the surface of the carrier through the substantially same distance.

Moreover, in this method, it is also preferred that the carrier includes a carrier body having a surface thereof, and a coating made of a calcium phosphate based compound and provided on the surface of the carrier body. According to this feature, it is possible to adjust the density of the carrier having immobilized antigens or antibodies so as to be the optimum condition for the agglutination reaction.

In this case, it is preferred that the carrier is produced by colliding porous particles of the calcium phosphate based compound to the carrier body. This makes it possible to easily and reliably form the vicinity of the surface of the carrier into dense structure.

Further, in this case, it is also preferred that the porous particles are produced by agglutination bonding of primary particles of the calcium phosphate based compound. This makes it possible to more easily form the vicinity of the surface of the carrier into dense structure.

Moreover, in this method, it is also preferred that the antibodies are IgG. This makes it possible to increase the degree of selection of antigens.

According to the present invention, there is provided a carrier having immobilized antigens or antibodies, comprising a carrier having a substantially spherical shape and having a surface, in which at least the surface of the carrier is formed of a calcium phosphate based compound; antiligands provided on and surrounding the surface of the carrier; a blocking layer formed of a protein having low interaction with antigens or antibodies, the blocking layer being formed on a portion of the surface of the carrier where the antiligands are not provided, and the blocking layer being formed subsequent to the providing of the antiligands; and antigens or antibodies each having a portion that is irrelevant to the antigen-antibody reaction on which a ligand is provided, the antigens or antibodies being immobilized to the surface of the carrier through bonding between the ligands and the antiligands with the blocking layer effectively preventing antigens or antibodies from being directly absorbed to the surface without bonding between the ligands and the antiligands.

Moreover, according to the present invention, there is provided a method of manufacturing a carrier having immobilized antigens or antibodies according to prevent invention, the method comprising providing the antiligands on and surrounding the surface of the carrier having a substantially spherical shape; forming the blocking layer of a protein having low interaction with antigens or antibodies on the portion of the surface of the carrier where the antiligands are not provided subsequent to the providing of the antiligands; and immobilizing the antigens or antibodies each having a portion that is irrelevant to the antigen-antibody reaction to the surface of the carrier which is formed of a calcium phosphate based compound through bonding between the ligands and the antiligands.

Still further, according to the present invention, there is provided a carrier having immobilized antigens or antibodies, comprising a carrier having a substantially spherical shape and having a surface, wherein at least the surface of the carrier is formed of a calcium phosphate based compound; antiligands provided on the surface of the carrier; a blocking layer formed of a protein having low interaction with antigens or antibodies and having a metallic ion which has been subjected to a treatment for removing or reducing the metallic ion, the blocking layer being located on at least a portion of the surface of the carrier where the antiligands are not provided; and antigens or antibodies each having a constant region on which a ligand is provided, each of said antigens or antibodies being immobilized to the surface of the carrier through bonding between the ligands and antiligands with the blocking layer effectively preventing antigens or antibodies from being directly absorbed to the surface without bonding between the ligand and the antiligands.

These and other objects, structures and advantages of the present invention will become apparent when the following description of the preferred embodiments and examples are considered taken in conjunction with the appended drawing.

BRIEF DESCTIPTION OF THE DRAWING

FIG. 1 is a graph which shows an amount of adsorption of antigens in each of carriers having immobilized antibodies of the Example and the respective Comparative Examples, and a carrier obtained by the control.

DETAILED DESCRIPTION OF THE PREFERRED EMBODIMENTS

After repeated studies and considerations, the inventors of the present invention have reached to supposition that when the antigens or antibodies are simply immobilized (adsorbed) to a carrier, the antigens or antibodies are brought into a condition that is difficult to assist the antigen-antibody reaction.

In more detail, reacting portions of the immobilized antigens or antibodies (hereinafter, simply referred to as "reacting portions") for antibodies or antigens (bonding objects) in a sample to be examined are adsorbed by the surface of the carrier, so that they can not exhibit a sufficient bonding ability for the bonding objects.

In view of the above, the inventors have conceived that if antigens or antibodies can be immobilized to a carrier with the state that their reacting portions are not adsorbed by the surface of the carrier, it may be possible to obtain a carrier having immobilized antigens or antibodies having a high bonding ability to the bonding objects.

The present invention has been made in view of the above conception.

Hereinbelow, an explanation will be made with regard to the preferred embodiments of the present invention. In this regard, it is to be noted that the following description will be made based on the exemplary case where antibodies are immobilized to a carrier, but it goes without saying that this is also applicable to the case where antigens are immobilized to a carrier.

In the carrier having immobilized antibodies of the present invention, antibodies are immobilized to a carrier through respective portions thereof which are irrelevant to their antigen-antibody reaction, and at least a part of a portion of the surface of the carrier to which the antibodies are not immobilized is covered with a protein.

Specifically, the inventors have made repeated studies and researches for solving the problem mentioned above, and with this result, they have reached to a conclusion that antibodies should be immobilized to a carrier through respective portions thereof which are irrelevant to the antigen-antibody reaction, in particular antibodies should be immobilized to a carrier through ligands and antiligands at that portions. In this way, a bonding portion (reacting portion) of each antibody to the antigen is difficult to be directly adsorbed to or contacted with the surface of the carrier, so that it is believed that the bonding ability to the antigen (bonding ability) which is possessed by the antibody becomes difficult to be lost.

Therefore, according to the present invention, it is possible to obtain a carrier having immobilized antibodies which has a high bonding ability against antigens, in particular specific antigens against the antibodies carried by the carrier.

Here, it is to be noted that the shape of the carrier of the present invention is not limited to a specific shape, and various shapes such as spherical shape or flattened shape may be employed. If the carrier is formed into a spherical shape, it is easy to immobilize antibodies to a carrier with high uniformity. Further, if the carrier is formed into a flattened shape, it is easy to observe the agglutination reaction with naked eyes since the agglutination is easy to occur.

When a carrier having a spherical shape is used, it is preferable that the average diameter is in the range of 1 to 100 μm, and more preferably in the range of 3 to 20 μm. When the average diameter is in this range, it is possible to obtain a high antibody carrying ability, and it is also possible to confirm the agglutination reaction easily. If the particle size of the carrier is too large, there is a case that agglutination is hard to occur. On the other hand, if the particle size of the carrier is too small, an interaction between carriers becomes strong, thus resulting in the case that agglutination of unspecific carriers becomes easy to occur.

In the present invention, the carrier is constituted from a calcium phosphate compound, and preferably at least a part of the surface of the carrier is constituted from a calcium phosphate compound. The present inventors have found that such calcium phosphate compounds can appropriately adsorb antiligands. Further, such calcium phosphate compounds have excellent agglutinativity.

Examples of such a carrier include a carrier whole of which is made of a calcium phosphate compound, and a carrier which is obtained by covering or coating a carrier body made of a resin or ceramics or the like with a calcium phosphate compound.

Among these, a carrier which is obtained by covering or coating a carrier body with a calcium phosphate compound, that is a carrier comprised of a carrier body and a coating layer of a calcium phosphate compound provided on the outer surface of the carrier body. When such a carrier is used, the following three advantages are realized.

(1) It is easy to adjust the density of each carrier to an optimum level for occurrence of agglutination reaction of the carriers having immobilized antibodies.

(2) In such a carrier, the carrier body before the application of the coating of the calcium phosphate compound or the carrier after the manufacturing can be colored with a coloring matter such as pigment or dye. Use of such a colored carrier increases visibility of the carrier.

(3) As described later, it is preferable that the carrier used in this invention has a dense coating layer, that is the outer surface of the carrier is formed into a considerably smooth surface. In a carrier obtained by covering a carrier body with a calcium phosphate compound, it is comparatively easy to obtain such a smooth outer surface.

It is preferable that the density of such a carrier is in the range of 0.7 to 2.0 g/cm$^3$, and more preferably in the range of 0.9 to 1.2 g/cm$^3$. This makes it possible for the carrier having immobilized antibodies to cause agglutination reaction in water (or in an aqueous solution).

Further, in such a carrier, a portion in the vicinity of the outer surface may be either of dense or porous, but it is preferable that the potion is dense, that is the surface is formed into a relatively smooth surface. In this way, in the obtained carrier having immobilized antibodies, it is possible to immobilize respective antibodies with the state that their antigen bonding portions are far from the surface of the carrier through substantially the same distance. Namely, it is possible to reduce restriction for three-dimensional positions of the respective antibodies which are likely to be affected by the shape of the outer surface of the carrier. As a result, antigens (bonding objects) in the sample to be examined will be surely bonded with the antibodies.

In this connection, it is to be noted that when a carrier obtained by covering a carrier body with a calcium phosphate compound is used, the coating layer of the calcium phosphate compound should be formed into a dense structure.

As for the calcium phosphate compound that can be used in this invention, various compounds having a Ca/P ratio of 1.0 to 2.0 can be used. Examples of such compounds include $Ca_{10}(PO_4)_6(OH)_2$, $Ca_{10}(PO_4)_6F_2$, $Ca_{10}(PO_4)_6C_2$, $Ca_3(PO_4)_2$, $Ca_2P_2O_7$, $Ca(PO_3)_2$, $CaHPO_4$, and the like. Mixtures of two or more kinds of these compounds may also be used.

Among these, a calcium phosphate compound containing hydroxyapatite ($Ca_{10}(PO_4)_6(OH)_2$) as a major component thereof is most preferable. Hydroxyapatite has especially excellent carrying ability of antiligands and it has also excellent agglutinativity.

Further, when fluoro apatite ($Ca_{10}(PO_4)_6F_2$) is used, it is preferred that the content of fluorine in all calcium phosphate based compounds is less than 5 wt %. By doing so, elution of fluorine from the carrier can be prevented, so that it is possible to prevent efficiency of the antigen-antibody reaction from being lowered.

Note that these calcium phosphate compounds may be synthesized by a known wet synthesizing method or dry synthesizing method.

Further, in this case, the calcium phosphate compound may contain substances (raw materials or the like) that can still remain in the synthesizing process or secondary reaction products which are produced in the synthesizing process and the like.

As described above, antibodies are immobilized to such a carrier through antiligands which are carried by the carrier and ligands which are bonded to the antibodies.

An antiligand of the type that has a property to be adsorbed to a calcium phosphate compound is preferably used. Namely, it is preferable to use an antiligand of the type that can be adsorbed to the surface of the carrier. By using such an antiligand, it becomes possible to have the carrier to carry antiligands by a simple method such as contacting the antiligands with the carrier (described later).

Further, it is preferable that the antiligand can be specifically bonded to a ligand bonded to the antibody.

From this viewpoint, avidin (including derivatives thereof) or streptavidin or the like is preferably used for the antiligand. Among these, avidin is most preferred for the antiligand.

The inventors have found that avidin can be especially effectively adsorbed to calcium phosphate based compounds. In addition, avidin has an especially high bonding ability to a ligand (in particular, biotin) in a specific manner.

On the other hand, it is preferred for a ligand that it can be satisfactorily bonded to an antibody. Further, it is also preferable that it has affinity to the antiligand. Such a ligand can be reliably bonded with the antiligand. Therefore, by contacting the antibody to which the ligand is bonded with the carrier on which the antiligand is carried, the ligand is bonded with the antiligand, so that the antibody is immobilized to the carrier. In other words, when an antibody to which a ligand is bonded is made contact with a carrier on which an antiligand is carried, the antibody is immobilized to the carrier through the ligand and the antiligand.

From this viewpoint, biotin, protein A or protein G, or the like is preferably used for the ligand. Among these, biotin is most preferred. This is because biotin can be easily bonded to an antibody (in particular, to a constant region thereof). In addition, biotin has an especially high bonding ability to an antiligand (in particular, to avidin) in a specific manner.

Further, it is preferred that when a ligand is bonded to an antibody, the ligand is bonded to the constant region of the antibody. When the ligand is bonded to the constant region of the antibody, the constant region of the antibody is located at a position relatively near from the carrier while the antigen bonding portions (reaction portions) of the antibody are located at positions relatively far from the carrier. That is, the antigen bonding portions of the antibody are located at positions that are outwardly protruded from the surface of the carrier. Accordingly, around the vicinity of the antigen bonding portions of the antibody, a space that is sufficient for the antigen-antibody reaction is secured. In addition, it is possible to prevent that the antigen bonding portions of the antibody are contacted with the surface of the carrier by adsorption by the carrier. For these reasons, when the ligand is bonded to the constant region of the antibody, the antigens in the sample to be examined are brought into contact with the antibody appropriately.

Note that the bonding of the ligand to the antibody may be carried out by means of a known labeling method. Further, commercially available markers, e.g. "biotin labeled anti-human immunoglobulin G antibody (A-130BC)" produced by American Qualex Co., Ltd. may be employed.

In particular, in the present invention, by using a combination in which avidin is used for an antiligand which is to be carried by a carrier and biotin is used for a ligand which is to be bonded to an antibody, it is possible to obtain an especially excellent effect. This is because avidin has a binding site in which one molecule of avidin can be bonded to four molecules of biotin. For this reason, avidin can be bonded to biotin in the amount of 4 times thereof, so that the carrier can support so many antibodies through the avidin-biotin bonding.

In this connection, it is to be noted that in this specification, the terms "antiligand" and "ligand" mean substances that form a pair which can be bonded with each other in a specific manner. Therefore, these terms can have meaning only when they are used as the pair, and they do not have any meaning when used alone.

Further, it is also to be noted that in the present invention, any antibodies such as IgG, IgM, IgA, IgE, and the like may be used. Among these antibodies, IgG is most suitable for the antibodies. This is because IgG can be easily produced. Further, when IgG is used, kinds of antigen that can be detected by the carrier having immobilized antibodies according to the present invention is increased.

Further, in the carrier having immobilized antibodies, a portion of the surface of the carrier to which the antibodies are not immobilized, namely, at least a part of a portion of the surface of the carrier which is a region other than the region on which antiligands are carried (preferably all of such a portion) is covered with a protein (that is, a blocking agent) which has a low interaction with the antigens or antibodies.

In this regard, the term "antigens or antibodies" include not only antigens or antibodies which are to be immobilized to a carrier according to the present invention but also other general antigens or antibodies. Further, the language "low interaction with the antigen or antibody" means that the ability for adsorbing antigens or antibodies or the ability for bonding antigens or antibodies is absent or such ability is extremely low.

By providing such a protein coating, it becomes possible to effectively prevent the antibodies from being unspecifically adsorbed to the carrier when the antibodies are immobilized to the carrier. Namely, it is possible to prevent that the antibodies are adsorbed to the carrier directly without using the ligands and antiligands. As a result, the carrier having immobilized antibodies can have an increased antigen bonding ability.

Further, when detection for antigens which have a characteristic to be adsorbed to a calcium phosphate compound is carried out using the obtained carrier having immobilized antibodies, it is possible to prevent the antigens from being unspecifically bonded (adsorbed) to the carrier.

As for the protein, any protein having a characteristic to be adsorbed to a calcium phosphate compound is preferably used. Namely, it is preferable that a portion of the surface of the carrier to which the antibodies are not immobilized is covered by a protein by the adsorption of the carrier to the surface of the carrier. By using such a protein, it becomes possible to cover the outer surface of the carrier with the protein by means of a simple method such as only contacting the protein to the carrier (described later in more detail).

Examples of such a protein include metallic proteins such as casein, transferin, ferredoxins, and the like, albumin, gelatin, vitellin, phosvitin, and the like. Among these proteins, casein, albumin and gelatin are preferably used. These proteins have excellent adsorptivity to calcium phosphate compounds. Further, among these proteins, casein is most preferable, since casein has excellent adsorptivity to calcium phosphate based compounds and has extremely small interaction with antibodies.

Further, when a protein having a metallic ion such as metallic protein or the like is used, it is preferable that the protein has been subjected to a treatment for removing or reducing the metallic ion. By this treatment, the protein coating for the surface of the carrier can be made to a substantially complete one.

As for a method for removing the metallic ion, a method in which a solution of such a protein (blocking agent solution) is processed by a chelating agent such as ethylene-diamine tetra-acetate (EDTA) can be mentioned. In this case, as for an example of the treatment of the protein solution with the chelating agent, the following method can be mentioned. Namely, after a chelating agent is added to a protein solution, the chelating agent is removed from the protein solution by means of a gel filtering, an ultrafiltration, or a dialylsis, or the like.

Further, in the carrier having immobilized antibodies, it is preferred that the antibodies have been subjected to a stabilizing treatment. By this treatment, the antibodies immobilized to the carrier are stabilized, so that a removal of an antibody from the carrier will be prevented.

Furthermore, if the stabilizing treatment is performed for the carrier after the surface of the carrier has been coated with a protein, there is also an advantage in that the protein becomes difficult to remove from the surface of the carrier.

In this case, it is preferred that such a stabilizing treatment is performed by treating the carrier with a stabilizing agent. This makes it possible to easily obtain a carrier having immobilized antibodies.

In the case where antibodies are immobilized to a carrier through ligands and antiligands, it is preferable to use, as the stabilizing agent, a cross-linking agent that couples either of the ligands or antiligands or both the ligands and the antiligands to the carrier. In this way, covalent bonding is formed between the carrier and either of the ligands or antiligands or both the ligands and the antiligands, so that it is possible to bond or immobilize them strongly. As a result, it is possible to prevent the antibodies from being removed from the carrier more reliably.

Various types of cross-linking agent can be used for the cross-linking agent, but it is especially preferable to use a bivalent cross-linking agent. By using such a bivalent cross-linking agent, it is possible to reliably stabilize the antibodies.

Examples of such a bivalent cross-linking agent include glutaraldehyde, p-benzoquinone, m-maleimide benzoic acid, N,N'-o-phenylenedimaleimide, and the like. One kind or a combination of two or more kinds of these compounds may be used.

Further, as for the stabilizing agent, bonding agents such as formaldehyde, silane coupling agents, and the like, osmium tetrachloride, and the like may be used.

Hereinbelow, a description will be made with regard to the manufacturing method of such a carrier having immobilized antibodies, that is a method for immobilizing antibodies.

First, prior to the manufacturing of the carrier having immobilized antibodies, a carrier as described above is prepared.

A carrier of which outer surface is constituted from or coated with a calcium phosphate compound can be obtained by colliding porous particles of a calcium phosphate compound (hereinafter, referred to as "calcium phosphate compound particles") to a carrier body. According to this method, calcium phosphate compound particles are crushed and then formed into relatively smaller size particles when collided to the carrier body, and such smaller size particles cover the surface of the carrier body. As a result, the portion in the vicinity of the outer surface can be formed into a dense structure easily and reliably.

From this viewpoint, it is preferable to use calcium phosphate compound particles which are produced by agglutination bonding of primary particles thereof. Such calcium phosphate compound particles are easily formed into smaller particles when collided to the carrier body, so that it becomes possible to form the portion in the vicinity of the outer surface of the carrier to a dense structure more easily and reliably.

In this case, when the average particle size of the calcium phosphate compound particles to be collided is set to be in the range of 0.1 to 50 μm, the effect described above will be more conspicuous. In this connection, it is to be noted that if the average particle size of the calcium phosphate compound particles is too large, there is a case that crush will not occur appropriately when the particles are collided with the carrier body.

The calcium phosphate compound particles may be either one of unsintered bodies or sintered bodies (that is, ceramics), but it is preferable to use unsintered bodies or sintered bodies that were sintered at a relatively low temperature (200 to 900° C.).

Note that the manufacturing method of the calcium phosphate compound particles is not limited to the above described method, and it is also possible to manufacture calcium phosphate compound particles by the following known method.

Namely, crystalline particles (primary particles) of a calcium phosphate compound which was synthesized by a know wetting method is used as a raw material for the calcium phosphate compound particles. A slurry in which the raw material particles are suspended is granulated into secondary particles by means of a direct spray drying method and the like. Alternatively, the slurry may be formed into secondary particles by means of a direct spray drying method and the like after adding a viscosity adjuster and organic compound particles or fibers which will be dissipated by heating into the slurry. Since the secondary particles are formed into porous particles, it is possible to use such secondary particles as they are to produce a carrier.

Further, in the case where calcium phosphate compound particles having higher porosity are preferred, they can be manufactured by the following method. First, the secondary particles described above are suspended in a solution to form a slurry again, and the slurry is formed into a block by means of a wet molding or a dry molding under pressure. In this step, an organic compound which will be dissipated during the subsequent sintering step may be added to form pores. Alternatively, the diameter of pore may be controlled by adjusting other condition such as a sintering temperature or the like without adding such an organic compound. Next, thus obtained block is sintered at a temperature of 400 to 1300° C. In this regard, if the sintering temperature is less than 400° C., there is a case that the dissipation of the organic compound and the sintering of the block can not be sufficiently carried out. On the other hand, if the sintering temperature exceeds 1300° C., there is a case that the sintered body becomes too dense or the calcium phosphate compound is decomposed. Thereafter, thus obtained sintered block is crushed and then classified to obtain particles having a desired diameter. In this regard, it is to be noted that the pore diameter of the calcium phosphate compound particles may be adjusted by appropriately changing the particle size of the primary particles, the viscosity of the slurry, and the kind of additive and the like.

(1) Next, antiligands are carried on the surface of each of carriers. This can be done by treating carriers with an antiligand solution. For this purpose, the carriers may be put in the antiligand solution to mix them, and the antiligand is thereby provided on and surrounds the surface of the carrier.

In this case, it is preferred that the concentration of the antiligand solution is in the range of 0.001 to 100 mg/mL, and more preferably in the range of 0.01 to 10 mg/mL. Further, it is also preferred that the amount of the antiligands in the antiligand solution per the carriers of 1 g is in the range of 0.01 to 100 mg. Furthermore, it is also preferred that the volume of the antiligand solution per the carriers of 1 g is in the range of 1 to 100 mg. Moreover, it is also preferred that the pH of the antiligand solution is in the range of 5.5 to 9. By adopting these factors, it becomes possible to appropriately let the antiligands to be carried on the respective carriers.

(2) Next, the outer surface of each carrier is coated or covered with a protein (that is, a blocking treatment is carried out). This can be done by treating the carriers with the protein solution (that is, the blocking agent solution). For this purpose, carriers may be put in the protein solution to mix them.

In this case, it is preferred that the concentration of the protein solution is in the range of 0.1 to 100 mg/mL, and more preferably in the range of 1 to 50 mg/mL. Further, it is also preferred that the amount of the protein in the protein solution per the carriers of 1 g is in the range of 1 to 100 mg. Furthermore, it is also preferred that the volume of the protein solution per the carriers of 1 g is in the range of 1 to 100 mL. Moreover, it is also preferred that the pH of the protein solution is in the range of 5.5 to 9. By adopting these factors, it becomes possible to appropriately cover the carriers with the protein.

(3) Next, antibodies to which ligands are bonded are immobilized to the carriers. This can be done by mixing the carriers on which the antiligands are carried with an antibody solution containing the antibodies to which the ligands are bonded.

In this case, it is preferred that the concentration of the antibody solution is in the range of 0.001 to 10 mg/mL, and more preferably in the range of 0.01 to 1 mg/mL. Further, it is also preferred that the amount of the antibodies in the antibody solution is in the range of 0.01 to 100 mg per the carriers of 1 g. Furthermore, it is also preferred that the volume of the antibody solution per the carriers of 1 g is in the range of 1 to 100 mL. Moreover, it is also preferred that the pH of the antibody solution is in the range of 5.5 to 9. By adopting these factors, it becomes possible to appropriately immobilize the antibodies onto the carriers.

(4) Next, the carriers to which the antibodies are immobilized are stabilized. This can be done by treating the carriers to which the antibodies are immobilized with a stabilizing agent. For this purpose, the carriers to which the antibodies are immobilized may be mixed with a stabilizing agent (immobilizing agent).

In this case, it is preferred that the concentration of the stabilizing agent in the stabilizing agent solution is in the range of 0.01 to 1 mg/mL, and more preferably in the range of 0.05 to 0.1 mg/mL. Further, it is also preferred that the amount of the stabilizing agent in the stabilizing agent solution is in the range of 0.1 to 10 mg per the carriers of 1 g. Furthermore, it is also preferred that the volume of the stabilizing agent solution per the carriers of 1 g is in the range of 1 to 100 mL. Moreover, it is also preferred that the pH of the antibody solution is in the range of 5.5 to 9. By adopting these factors, it becomes possible to appropriately stabilize the antibodies that have been immobilized to the carriers, so that the obtained carrier having the immobilized antibodies will be difficult to deteriorate with the elapse of time.

The antibodies are immobilized to the carriers through the above processes, namely, the carriers having the immobilized antibodies can be obtained.

In the present invention, another operation that is the same as the process (4) described above may be done before or after the above process (2). Further, another operation that is the same as the process (2) described above may be done before or after the above process (4). Furthermore, the processes (2) and (4) may be omitted.

Furthermore, it is preferred that these processes (1) to (4) are carried out at a room temperature (e.g. 0 to 40° C.), for example.

Although the foregoing description was made based on the exemplary case where antibodies are used, the present invention can be applied to the case where antigens are used.

When the present invention is applied to carriers having immobilized antigens, examples of antigens that are to be immobilized to the carriers include viruses leading to infections such as influenza, Japanese encephalitis, breakbone fever, rubella, rubeola, mumps, and the like, and bacteria, and the like.

In the foregoing, the carriers having immobilized antigens or antibodies of the present invention and the manufacturing method thereof were described, but the present invention is not limited thereto.

For example, in the manufacturing method of the carriers having immobilized antigens or antibodies of the present invention, additional one or more processes may be added as needed for various purposes.

EXAMPLES

Next, this invention is described in detail in accordance with the actual examples. However, this invention is not limited to these examples.

Example

A carrier having immobilized antibodies was obtained as in the follows.

1. Manufacture of Carrier

Prior to immobilization of antibodies to a carrier, the carrier was prepared as in the following.

First, 50 g of nylon beads (having average particle size of 5 µm and density of 1.02 g/cm$^3$) and 10 g of hydroxyapatite particles (having Ca/P ratio of 1.67, average particle size of 5 µm, specific surface of 45 m$^2$/g and average pore size of 600 Å) were prepared.

Next, these nylon beads and hydroxyapatite particles were introduced into NARA hybridization system (manufactured and sold by Nara Machinery Co., Ltd with product code of NHS-1 having a power rating of 5.5 kW and a current rating of 23 A) and the machine was operated at 8,000 rpm at temperatures ranging from 32 to 50° C. for 5 minutes. As a result, nylon beads (complex particles) each having a surface coated with hydroxyapatite were obtained.

In this regard, it is to be noted that the obtained complex particle had average particle size of 5.8 µm and density of 1.13 g/cm$^3$. In addition, the average thickness of the coating layer made of hydroxyapatite of such complex particles was 0.45 µm.

2. Manufacture of Carrier Having Immobilized Antibodies

In the operation described hereinbelow, the room temperature was 20° C.

Prior to the explanation of immobilization of antibodies to the carrier, explanation is made with the regard to casein dissolved in a casein solution which was used in the following process <2>. Namely, casein dissolved in casein solution to be used in the following process <2> had been subjected to a treatment in advance to remove calcium ion contained in casein. The treatment to remove calcium ion was carried out as in the following.

(1) First, 2.5 ml of 40 mg/ml casein solution was prepared and 0.5 ml of 500 mM EDTA solution was added to the casein solution. As a result, 25 ml of casein/EDTA mixed solution in which the concentration of casein was 4 mg/ml and the concentration of EDTA was 10 mM was obtained. In this regard, it is to be noted that the casein solution prepared was obtained by adjusting the concentration of "Block Ace" (trade mark) manufactured and sold by Snow Bland Milk Products Co., Ltd.

(2) Next, in order to remove EDTA from the mixed solution, the mixed solution was subjected to gel filtration chromatography. Further, the buffer of the casein solution was exchanged in addition to the removal of EDTA described above. (At this time, before and after the gel filtration chromatography, the concentration of calcium ion in the mixed solution and the concentration of calcium ion in a resultant casein solution were measured, respectively. As a result, the concentration of calcium ion in the casein solution decreased to ⅙ or less. From the result, it was confirmed that most of the calcium ion contained in casein was removed. In this regard, it is to be noted that the concentration of the calcium ion was obtained by measuring the absorbance of the solution at 423 nm.)

(3) Finally, the obtained casein solution was concentrated such that the casein concentration thereof was approximately 4 mg/ml.

<1> 1 ml of 0.1 mg/ml avidin solution (manufactured and sold by Pierce Chemical Company) was added to 10 mg of the complex particles obtained as described above.

And then, this mixture was mixed at a room temperature for 60 minutes and centrifuged at 1,000 rpm for 5 minutes to remove the excess avidin. Thereafter, thus obtained complex particles were rinsed.

<2> Next, 1 ml of 4 mg/ml casein solution adjusted in the manner described above was added to the complex particles obtained in <1>.

And then, the complex particles and the casein were reacted together at a temperature of 37° C. for 60 minutes and they were centrifuged at 1,000 rpm for 5 minutes to remove the excess casein. Thereafter, thus obtained complex particles were rinsed.

<3> Next, 1 ml of 0.01 mg/ml biotin-labeled (conjugated) anti-human immunoglobulin G antibody (goat serum) solution was added to the complex particles obtained in <2>. In this regard, it is to be noted that the biotin-labeled anti-human immunoglobulin G antibody (manufactured and sold by American Qualex Co., Ltd.) was produced by bonding biotin to the constant region of the IgG.

And then, this mixture was mixed at a room temperature for 60 minutes and centrifuged at 1,000 rpm for 5 minutes to remove the excess antibody. Thereafter, thus obtained complex particles were rinsed.

<4> Next, 1 ml of 1 mg/ml glutaraldehyde (manufactured and sold by Wako Pure Chemical Industries., Ltd) solution was added to the complex particles obtained in <3>.

Then, the complex particles and the glutaraldehyde (bivalent cross-linking agent) were reacted together at a temperature of 37° C. for 30 minutes and centrifuged at 1,000 rpm for 5 minutes to remove the excess glutaraldehyde. Thereafter, thus obtained complex particles were rinsed.

<5> Next, 1 ml of 4 mg/ml casein solution was added to the complex particle obtained in <4>.

And then, this mixture left at a temperature of 37° C. for 60 minutes and centrifuged at 1,000 rpm for 5 minutes to remove the supernatant.

As a result, carriers each having immobilized antibodies were obtained, in which anti-human IgG antibodies (IgG) were immobilized to the surface of each nylon bead coated with hydroxyapatite through avidin and biotin.

In this regard, it is to be noted that phosphate buffer salt solution (pH 6.8) was used to adjust the avidin solution, the biotin-labeled anti-human immunoglobulin G antibody solution and the glutaraldehyde solution, and to rinse the complex particles in each treatment described in <1> to <5> in the above.

Comparative Example 1

A carrier having immobilized antibodies in which the antibodies were directly immobilized to the carrier without using avidin and biotin was manufactured. Such carrier having immobilized antibodies was manufactured as in the following.

First, 10 mg of nylon beads each having a surface coated with hydroxyapatite were prepared. The prepared beads were the same as those described above.

Next, 1 ml of 0.01 mg/ml anti-human immunoglobulin G antibody (goat serum) solution was added to these complex particles. In this regard, it is to be noted that the anti-human immunoglobulin G antibody (manufactured and sold by Cappel, Inc.) was not conjugated with biotin.

And then, this mixture was mixed at a room temperature for 60 minutes and centrifuged at 1,000 rpm for 5 minutes to remove the excess antibodies. Thereafter, thus obtained complex particles were rinsed.

Next, 1 ml of 4 mg/ml casein solution was added to the complex particles obtained. The casein solution used was the same as that described above.

And then, the complex particles and casein were reacted together at a temperature of 37° C. for 60 minutes and centrifuged at 1,000 rpm for 5 minutes to remove the excess casein. Thereafter, thus obtained complex particles were rinsed.

Subsequent to these operations, the same operations as those described in <4> and <5> in the above were carried out to the complex particles in this order.

As a result, carriers each having immobilized antibodies were obtained, in which the anti-human immunoglobulin G antibodies (IgG) were immobilized to the surface of each nylon bead coated with hydroxyapatite without using avidin and biotin.

Comparative Example 2

A carrier having immobilized antibodies in which a protein A was carried by the surface of the carrier and the antibodies were immobilized to the carrier through the protein A was manufactured. Such carrier having immobilized antibodies was manufactured as in the following.

First, 10 mg of nylon beads each having a surface coated with hydroxyapatite were prepared. The prepared beads were the same as those described above.

The same operation as that described in <1> in the above was carried out to the prepared beads using 1 ml of 0.1 mg/ml protein A (manufactured and sold by Cappel, Inc.) solution in stead of using avidin solution. Subsequence to this operation, the same operation as that described in <2> in the above was also carried out to the beads in which the protein A had been carried.

Next, 1 ml of 0.01 mg/ml anti-human immunoglobulin G antibody (goat serum) solution was added to the obtained complex particles. In this regard, it is to be noted that the anti-human immunoglobulin G antibody (manufactured and sold by Cappel, Inc.) was not conjugated with biotin.

And then, this mixture was mixed at a room temperature for 60 minutes and centrifuged at 1,000 rpm for 5 minutes to remove the excess antibodies. Thereafter, the obtained complex particles were rinsed.

Subsequent to these operations, the same operations as those described in <4> and <5> in the above were carried out to the complex particles in this order.

As a result, carrier each having immobilized antibodies were obtained, in which the anti-human IgG antibodies (IgG) were immobilized to the surface of each nylon bead coated with hydroxyapatite through protein A.

In this regard, it is to be noted that a phosphate buffer salt solution (pH 6.8) was used to adjust the protein A solution.

(Control)

First, 10 mg of nylon beads each having a surface coated with hydroxyapatite were prepared. The prepared beads were the same as those described above.

Subsequent to this, the same operations as those described in <2>, <4> and <5> in the above were carried out to the prepared beads in this order.

As a result, a carrier which was manufactured only by covering the surface of the nylon bead coated with hydroxyapatite with casein and then stabilizing the casein with glutaraldehyde was obtained.

(Evaluation)

For each carrier having immobilized antibodies obtained by Example and Comparative Examples and the carrier obtained by Control, bonding ability with antigens was measured, respectively.

First, 1 ml of normal human serum (manufactured and sold by Rockland, Inc.) diluted to ten thousands times was added to 1 mg of each carrier having immobilized antibodies obtained by Example and Comparative Examples and the carrier obtained by Control, respectively.

Next, thus obtained each solution was mixed at a room temperature for 30 minutes and centrifuged at 1,000 rpm for 5 minutes to remove the excess serum. And then, each carrier having immobilized antibodies and the carrier were rinsed.

Next, 1 ml of 0.0005 mg/ml HRP (Horse Radish Peroxidase) labeled anti-human immunoglobulin G antibody (goat serum) solution was added to each carrier having immobilized antibodies and the carrier, respectively. In this regard, it is to be noted that in the HRP-labeled anti-human immunoglobulin G antibody (manufactured and sold by Cappel, Inc.), HRP was bonded to IgG.

Next, each carrier having immobilized antibodies and the carrier, and HRP-labeled anti-human immunoglobulin G antibody were reacted together at a room temperature for 30 minutes and centrifuged at 1,000 rpm for 5 minutes to remove the excess antibodies. And then, each carrier having immobilized antibodies and the carrier were rinsed.

Next, 0.5 ml of 0.3 mg/ml 3,3', 5,5'-tetramethylbenzidine solution (manufactured and sold by Moss Inc.) was added to each carrier having immobilized antibodies and the carrier, respectively, to make a color reaction at a room temperature for 30 minutes.

And then, each obtained solution was centrifuged at 1,000 rpm for 5 minutes to correct the 100 μL of supernatant thereof. 20 μL of 1N HCl was added to each obtained supernatant, respectively to stop the color reaction, and then absorbance thereof was measured at 450 nm, respectively.

In this regard, it is to be noted that phosphate buffer salt solution (pH 6.8) was used to adjust normal human serum, HRP-labeled anti-human immunoglobulin G antibody solution and 3,3',5,5'-tetramethylbenzidine solution, and to rinse the complex particles in each treatment described in the above.

The results of the measurements described above are shown in the following TABLE 1, and FIG. 1 is a graph which shows the results.

TABLE 1

| | Control | Protein A anti-Hu IgG Comp. Ex. 2 | Anit-Hu IgG Comp. Ex. 1 | Avidein-Biotin anti-Hu IgG Example |
|---|---|---|---|---|
| Absorbance (O.D. 450) | 0.132 | 0.208 | 0.389 | 2.498 |

As apparent from Table 1 and FIG. 1, in each carrier having immobilized antibodies obtained by respective Comparative Examples, only a few IgG antibodies contained in normal human serum (antigen) were bonded thereto. On the other hand, in the carrier having immobilized antibodies obtained by Example, a large amount of IgG antibodies contained in normal human serum were bonded thereto. This is supposed to result from the following reasons. Namely, in the carrier having immobilized antibodies obtained by Example, the antigen bonding portions (reaction portions) of each antibody immobilized to the carrier protrude outwardly from the surface of the carrier so that high bonding ability of antibody for antigens is maintained.

For this reason, it is confirmed that the carrier having immobilized antibodies obtained by Example has extremely high bonding ability with antigens.

Further, carriers each having immobilized antibodies were manufactured in the same manner as Example described above excepting that albumin and gelatin were respectively used in stead of casein as protein to coat the portion of a carrier where the antibodies were not immobilized. Furthermore, carriers each having immobilized antibodies were also manufactured in the same manner as Example described above excepting that p-benzoquinone, m-maleimide benzoic acid and N,N'-o-phenylenedimaleimide were respectively used instead of glutaraldehyde as a bivalent cross-linking agent (stabilizing agent) to stabilize the antibodies.

And then, for these manufactured carriers each having immobilized antibodies, the bonding ability thereof with antigens was measured in the same manner as described above. As a result, it was confirmed that all the carriers each having immobilized antibodies had extremely high bonding ability with antigens as was the case with Example.

EFFECTS OF THE INVENTION

As described above, according to the present invention, it is possible to immobilize antigens or antibodies to a carrier while maintaining high bonding ability with antigens or antibodies (which are bonding objects) contained in a sample to be examined.

Therefore, according to the present invention, it is possible to obtain a carrier having immobilized antigens or antibodies having high bonding ability with antigens or antibodies contained in a sample to be examined. Further, by using such a carrier having immobilized antigens or antibodies, it becomes possible to detect antigens or antibodies contained in a sample to be examined with high sensitivity so that the carrier having immobilized antigens or antibodies is extremely useful in diagnosis of various kinds of diseases such as infections and the like utilizing the antigen-antibody reaction.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2000-362762 (filed on Nov. 29, 2000) and Japanese Patent Application No. 2001-349447 (filed on Nov. 14, 2001) which are expressly incorporated herein by reference in their entireties.

What is claimed is:

1. A method of manufacturing a carrier having immobilized antibodies, comprising:
providing antiligands on and surrounding a surface of a carrier, the carrier having a substantially spherical shape and at least the surface of the carrier is formed of a calcium phosphate based compound;
treating a protein containing calcium ion to remove or reduce the calcium ion to thereby obtain a treated protein, the protein having low interaction with antigens or antibodies;
forming a blocking layer comprising the treated protein on at least a portion of the surface of the carrier where the antiligands are not provided subsequent to the providing of the antiligands on and surrounding the surface of the carrier; and
immobilizing antibodies to the surface of the carrier, each of the antibodies having a constant region on which a ligand is provided, and each of the antibodies is immobilized to the surface of the carrier by bonding between the ligands and antiligands, and the blocking layer effectively preventing antibodies from being directly absorbed to the surface without bonding between the ligand and the antiligands.

2. The method of manufacturing a carrier having immobilized antibodies as claimed in claim 1, wherein the antiligands are adsorbed by the surface of the carrier.

3. The method of manufacturing a carrier having immobilized antibodies as claimed in claim 1, wherein the ligands are bonded to constant regions of the antibodies.

4. The method of manufacturing a carrier having immobilized antibodies as claimed in claim 1, wherein the forming the blocking layer comprises letting the protein be adsorbed to the at least a part of the portion of the surface of the carrier.

5. The method of manufacturing a carrier having immobilized antibodies as claimed in claim 1, wherein the protein is casein.

6. The method of manufacturing a carrier having immobilized antibodies as claimed in claim 1, wherein the method further comprises, after the immobilizing, stabilizing the antibodies.

7. The method of manufacturing a carrier having immobilized antibodies as claimed in claim 6, wherein the stabilizing is carried out by treating the carrier with a stabilizing agent.

8. The method of manufacturing a carrier having immobilized antibodies as claimed in claim 6, wherein the stabilizing is carried out by treating the carrier with a cross-linking agent for bonding the antibodies to the ligands and/or antiligands.

9. The method of manufacturing a carrier having immobilized antibodies as claimed in claim 8, wherein the cross-linking agent is a bivalent cross-linking agent.

10. The method of manufacturing a carrier having immobilized antibodies as claimed in claim 1, wherein a portion of the carrier which is in the vicinity of the surface thereof is formed into a dense structure.

11. The method of manufacturing a carrier having immobilized antibodies as claimed in claim 1, wherein the carrier includes a carrier body having a surface, and a coating made of a calcium phosphate based compound is provided on the surface of the carrier body.

12. The method of manufacturing a carrier having immobilized antibodies as claimed in claim 11, wherein the carrier is produced by colliding porous particles of the calcium phosphate based compound to the carrier body.

13. The method of manufacturing a carrier having immobilized antibodies as claimed in claim 12, wherein the porous particles are produced by agglutination bonding of primary particles of the calcium phosphate based compound.

14. The method of manufacturing a carrier having immobilized antigens as claimed in claim 1, wherein the antibodies are IgG.

15. The method of manufacturing a carrier having inimobilized antibodies as claimed in claim 1, wherein the calcium ion is reduced in the protein.

16. The method of manufacturing a carrier having immobilized antibodies as claimed in claim 1, wherein the calcium ion is removed from the protein.

17. The method of manufacturing a carrier having immobilized antibodies as claimed in claim 5, wherein the calcium ion is reduced in the protein.

18. The method of manufacturing a carrier having immobilized antibodies as claimed in claim 5, wherein the calcium ion is removed from the protein.

19. A method of manufacturing a carrier having immobilized antibodies, comprising:
providing antiligands on and surrounding a surface of a carrier, at least the surface of the carrier being formed of a calcium phosphate based compound;
treating a protein containing calcium ion to remove or reduce the calcium ion to thereby obtain a treated protein, the protein having low interaction with antigens or antibodies;
forming a blocking layer comprising the treated protein on at least a portion of the surface of the carrier where the antiligands are not provided subsequent to the providing of the antiligands on and surrounding the surface of the carrier; and immobilizing antibodies to the surface of the carrier, each of the antibodies having a constant region on which a ligand is provided, and each of the antibodies is immobilized to the surface of the carrier by bonding between the ligands and antiligands, and the blocking layer effectively preventing antibodies from being directly absorbed to the surface without bonding between the ligand and the antiligands.

* * * * *